United States Patent
Brunel

(10) Patent No.: US 6,432,090 B1
(45) Date of Patent: Aug. 13, 2002

(54) DISPOSABLE INJECTION DEVICE DESIGNED TO BE PRE-FILLED

(75) Inventor: Marc Brunel, Toulouse (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/806,569

(22) PCT Filed: Sep. 30, 1999

(86) PCT No.: PCT/FR99/02326

§ 371 (c)(1),
(2), (4) Date: Apr. 2, 2001

(87) PCT Pub. No.: WO00/20057

PCT Pub. Date: Apr. 13, 2000

(30) Foreign Application Priority Data

Oct. 1, 1998 (FR) .............................................. 98 12309

(51) Int. Cl.⁷ .............................................. A61M 5/315
(52) U.S. Cl. ....................................... 604/236; 604/240
(58) Field of Search ............................... 604/181, 218, 604/231, 236, 240, 246, 249

(56) References Cited

U.S. PATENT DOCUMENTS

| | | | |
|---|---|---|---|
| 4,226,236 A | | 10/1980 | Genese |
| 4,398,544 A | * | 8/1983 | Nugent et al. ............... 604/236 |
| 4,639,250 A | | 1/1987 | Rycroft |
| 4,657,534 A | | 4/1987 | Beck |
| 5,611,785 A | * | 3/1997 | Mito et al. .................. 604/240 |
| 5,855,568 A | * | 1/1999 | Battiato et al. ............. 604/240 |
| 5,893,842 A | * | 4/1999 | Imbert ......................... 604/236 |

FOREIGN PATENT DOCUMENTS

| | | |
|---|---|---|
| DE | 847 473 | 8/1952 |
| DE | 1 909 794 | 9/1970 |
| DE | 2 008 751 | 8/1971 |
| EP | 0 111 796 | 6/1984 |
| EP | 0 112 574 | 7/1984 |
| EP | 0 150 681 | 8/1985 |
| EP | 0 191 508 | 8/1986 |
| EP | 0 588 148 | 3/1994 |
| EP | 0 602 883 | 6/1994 |
| EP | 0 720 857 | 7/1996 |
| FR | 2 208 684 | 6/1974 |
| FR | 2 330 413 | 6/1977 |
| FR | 2 347 055 | 11/1977 |
| FR | 2 412 320 | 7/1979 |
| WO | WO 84/04252 | 11/1984 |

* cited by examiner

Primary Examiner—Steven J. Ganey
(74) Attorney, Agent, or Firm—Young & Thompson

(57) ABSTRACT

The invention relates to an injection device comprising a syringe body (1, 13), which delimits a chamber which is designed to be filled with a liquid, and a unit (17) for distributing the liquid, comprising an end piece (17a) for closing off the chamber, which is extended by a locking male conical connection (17c), and can be displaced axially between a closing-off position of the said chamber and a position for injection of the liquid. According to the invention, the unit (17) for distributing comprises an intermediate connection (20), which is provided between the closing-off end piece (17a) and the male conical connection (17c). In addition, the syringe body (1, 13) comprises firstly a ring (3), which delimits two superimposed compartments with conjugated shapes, of the intermediate section (20) of the unit (17) for distributing, which are separated by a neck (9) which can permit axial displacement of the said intermediate section, and, secondly comprises a collar (12), which extends in the extension of the upper compartment (8), such as to accommodate the male conical connection (17c) of the said unit for closing off.

3 Claims, 4 Drawing Sheets

DISPOSABLE INJECTION DEVICE DESIGNED TO BE PRE-FILLED

The invention relates to an injection device of the single-use type, which is designed to be pre-filled with a dose of liquid, in particular a medicinal liquid, to be injected.

Single-use injection devices which are designed to be pre-filled comprise a syringe body, which is either provided with a base, in which there is sealed a needle, which is protected by a protective cap, or comprise a conical male locking connection, which makes it possible to fit onto the said syringe body a conical female locking connection, which supports an injection needle protected by a protective cap, the said conical connections defining an assembly which is commonly known as a "LÜER conical assembly".

The most conventional injection devices, known as the "wet needle" type, are of the type provided with a syringe body comprising a base, in which there is sealed an injection needle, which is closed off by means of a protective elastomer cap, which is provided with a inner blind bore contained in the base of the said cap, inside which the end of the said needle is forced, such as to guarantee the sealing of the injection device before injection takes place.

The first disadvantage of injection devices of this type consists in the fact that when the protective cap is put into place, the injection needle must be centred perfectly in relation to the bore in the said cap. However, in practice, this centring is sometimes approximate, such that fitting of the cap frequently leads to deterioration of the said cap or needle, resulting in significant numbers of production rejects.

In addition, according to this principle, the quality of the needle (sharpness, silicone coating), is systematically affected by the occurrence of friction of the point of the said needle against the inner wall of the blind bore in the cap, when the latter is forced on.

Finally, the liquid contained in these injection devices is necessarily in contact with the materials which constitute the injection needle and the protective cap, which, for certain types of liquid, can affect the conservation of the latter.

In order to eliminate these disadvantages, numerous injection devices known as the "dry needle" type have been designed, wherein the injection needle is isolated from the liquid contained in the syringe body until the moment of injection.

A first type of "dry needle" injection device is that which is commonly used in dentistry, and comprises a bottle, which contains the liquid to be injected, and is closed off by a membrane, and a double-point needle, which can be displaced axially relative to the said bottle, such as to pierce the membrane at the moment of injection. Injection devices of this type are described in particular in patents DE-847473, FR-2347055, U.S. Pat. No. 4,639,250, EP-602883, DE-2008751, DE-1909794.

This type of injection device has two sorts of disadvantages. In fact, firstly, the fact of needing a double-point needle leads to a increase in the cost price of these injection devices, derived firstly from the cost of the said needle itself, and secondly from the necessity of carrying out two sharpening operations instead of a single sharpening operation required for a conventional needle. In addition, for needles with a small diameter, it often happens that problems of coring arise, leading to the inclusion of particles of membrane inside the aperture of the needle, which either close off this aperture, or are injected together with the liquid.

A second type of "dry needle" injection device comprises a syringe body which accommodates two stoppers, which delimit the chamber containing the liquid, and onto which there is crimped a base, which either supports a needle, or is of the male conical connection type, the said syringe body additionally having a compartment which is provided with a duct for communication with the injection needle, which is disposed such as to be put into contact with the chamber only after the pistons have been displaced axially.

Injection devices of this type, which are described in particular in patents FR-2412320, FR-2208684, EP-191508, EP-588148 and EP-720857, make it possible to eliminate the disadvantages of the above-described injection devices. However, they themselves also have two disadvantages. In fact, firstly, the operation of crimping the base onto the syringe body is problematic, and requires particular care in order to guarantee perfect sealing between the said base and the said syringe body. In addition, and above all, injection devices of this type can be subject to accidental escape of the liquid contained in the chamber, resulting for example from expansion of the volume of gas contained in the said chamber, or from depressurisation, in particular during transport by air, which lead to axial displacement of the stopper for access to the compartment for discharge of the liquid.

A third type of "dry needle" injection device, described in particular in patentsEP-150681, EP-111796, FR-2330413 and WO-8404252, makes it possible to eliminate all of the above-described disadvantages. For this purpose, these injection devices comprise firstly a syringe body, which is provided with a chamber closed off by a rubber stopper, which contains a longitudinal through-bore, and secondly, a base which either supports a needle, or is of the male conical connection type, is mobile axially inside the bore of the said stopper, and is provided with ducts which are disposed such as to put the injection needle and the chamber into communication during axial displacement of the said base, which tends to thrust the latter into the stopper.

The present invention relates to an injection device of the locking conical assembly type, with a design similar to that of the injection devices of the third type described above, and the main objective of which is to provide an ergonomic injection device, which combines the advantages of these injection devices (sealing, guarantee against risks of accidental escape, etc), the activation of which for the purpose of an injection is carried out very simply, by means of a very natural gesture.

For this purpose, the invention relates to an injection device comprising a syringe body, which delimits a chamber which is designed to be filled with a liquid, in particular a medicinal liquid, and a unit for closing off the chamber and distributing the liquid, comprising an end piece for closing off the said chamber, which is extended by a locking male conical connection, provided with a duct for distribution of the liquid, the said unit for closing off and distributing being mobile axially between a position known as the closing-off position, in which the distribution duct is isolated from the chamber of the syringe body, and a position known as the injection position, in which the said distribution duct communicates with the said chamber.

According to the invention, this injection device is characterised in that:

the unit for closing off and distributing comprises an intermediate section, which is disposed between the closing-off end piece and the male conical connection, and is placed such as to extend in the extension of the syringe body;

the syringe body comprises a ring which is provided with a front wall, in which there is provided an axial opening for passage of the conical male connection, the said ring:

delimiting two inner, upper and lower compartments which are juxtaposed axially, each of which has a shape which is conjugated with the intermediate section of the unit for closing off and distributing, and can accommodate the said intermediate section, the said compartments being separated by axial stop units which can permit axial displacement of the intermediate section of one compartment towards the other compartment; and comprising in the extension of the front wall a sleeve which is threaded internally, and is designed to accommodate the male conical connection and to act as a fixed nut for assembly of a locking female conical connection which supports an injection needle.

Activation of an injection device of this type, for the purpose of the injection, is thus obtained automatically during assembly by screwing of a female conical connection onto the syringe body, which gives rise to axial displacement of the unit for closing off and distributing, of the upper compartment of the ring, towards the lower compartment of the said ring, resulting in the needle and the chamber of the syringe body being put into communication.

This activation is thus derived from simple fitting onto the injection device of a female conical connection which constitutes a conventional conical assembly, for example of the "LÜER" type.

In addition, the axial displacement of the unit for closing off and distributing is irreversible, owing to the fact that any further, inverse displacement, is subsequently prevented.

According to another characteristic of the invention, the ring has in its interior an annular neck which forms the top of two longitudinal divergent sections, and constitutes the axial stop means for separation of the upper and lower compartments, the intermediate section of the unit for closing off and distributing having a shape and dimensions which are conjugated with the upper compartment of the said ring.

Additionally, the injection device according to the invention advantageously comprises a closing-off stopper with dimensions which are suitable for being inserted in the syringe body, provided with a through bore which opens into the said syringe body at a countersink.

In addition, in this case, the unit for closing off and distributing has dimensions which are designed to be inserted in the bore in the closing-off stopper, and comprises a distribution duct containing a transverse branch, which is disposed such as to be positioned recessed from the countersink in the said closing-off stopper, in the closing-off position of the unit for closing off and distributing, and to extend into the said countersink, in the injection position of the said unit.

Other characteristics, objects and advantages of the invention will become apparent from the following detailed description provided with reference to the attached drawings, which represent a preferred embodiment, by way of non-limiting example. In these drawings.

Figure 1:
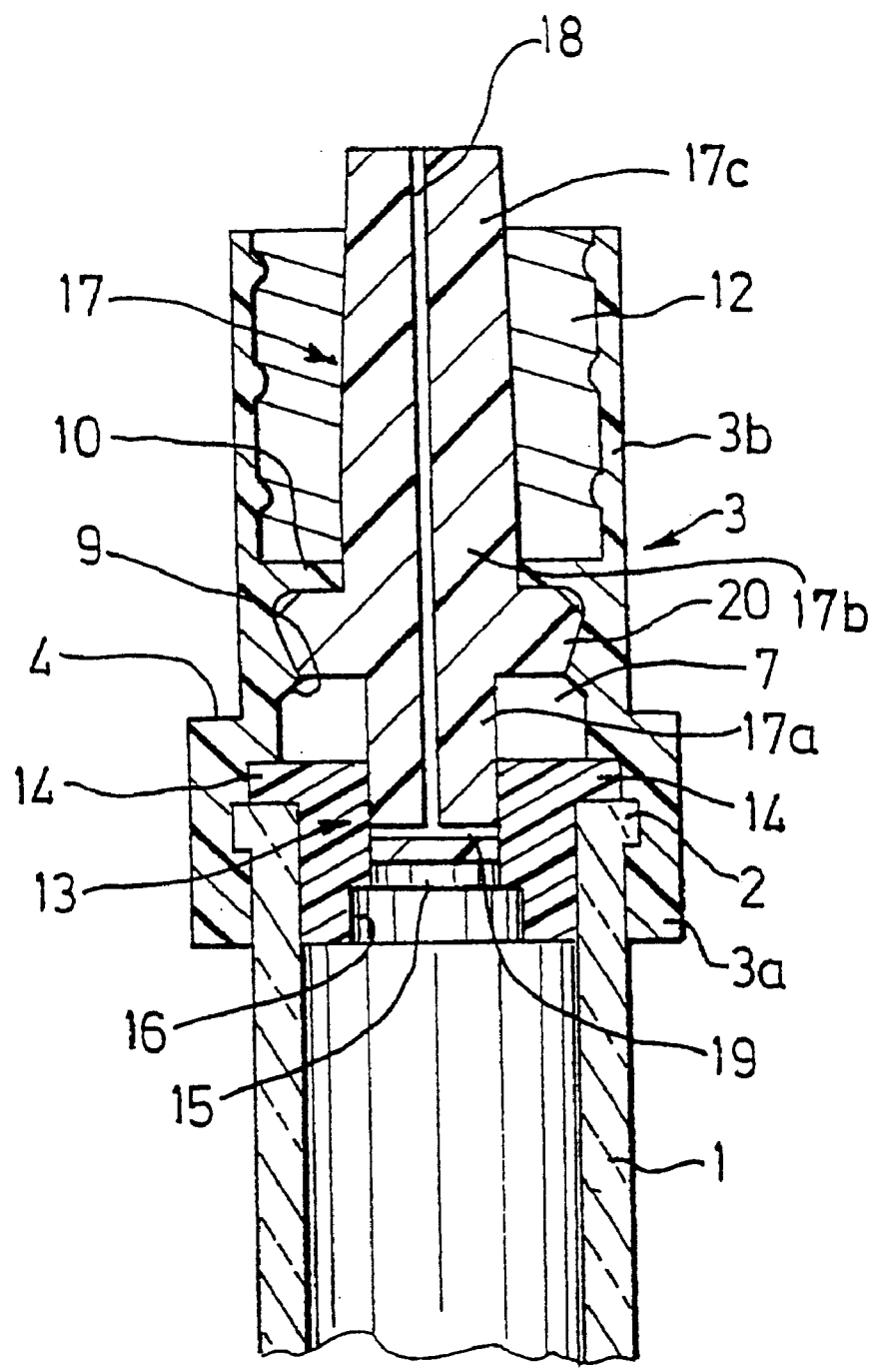
FIG. 1 is a longitudinal axial cross-section of an injection device according to the invention.

The injection device represented in FIG. 1 is of the single-use type, i.e. it is designed to be filled with a liquid to be injected. It should be noted that although the injection device as represented does not have a protective case, which is designed to make it possible to protect the needle, whilst avoiding any risks of being pricked, after injection has taken place it can be equipped in a known manner with any protective case of a conventional type which fulfils this function.

This injection device comprises firstly a conventional syringe body, containing a cylindrical tube 1, which is provided with an outer collar 2 at one of its ends.

This injection device additionally comprises a ring 3, which is designed to be fitted onto the end section of the cylindrical tube 1.

This ring 3 consists longitudinally of two cylindrical sleeves 3a, 3b, with different outer and inner diameters, which are separated by respective outer 4 and inner 5 shoulders.

The first sleeve 3a, which has the larger diameter, is designed to be fitted along its longer length onto the end section of the cylindrical tube 1 of the syringe body. In its interior, this sleeve 3a has a bore 6 which is divided longitudinally into four sections, which consist in succession of:

a first end section 6a, which is designed to be presented opposite the end of the syringe body during fitting of the ring 3, and has a frusto-conical shape defining a ramp, which can facilitate this fitting;

a first intermediate section 6b, which has a cylindrical shape with an inner diameter which is conjugated with the outer diameter of the cylindrical tube 1;

a second intermediate section 6c, with a toric shape, which is designed to be clipped onto the collar 2 of the cylindrical tube 1; and a fourth section 6d, for joining with the second sleeve 3b, with a cylindrical shape which has an inner diameter slightly smaller than that of the first intermediate section 6b.

The second sleeve 3b is itself divided internally into two longitudinal sections, which are separated by an intermediate transverse wall 10, provided with an axial aperture 11.

The first, lower one of these sections, which is separated from the joining section 6d of the first sleeve 3a by the inner shoulder 5, is itself divided longitudinally into two superimposed compartments 7, 8 with the same height, by an annular neck 9 which forms the top of two longitudinal divergent sections 9a, 9b:

a lower compartment 7, which, in the lower extension of the first divergent section 9a, has a cylindrical section for joining with the section 6d of the first sleeve 3a; and an upper compartment 8, which is delimited laterally by the second divergent section 9a, and is connected to the intermediate wall 10, by a divergent section which is parallel to the first divergent section 9a, and thus has a cross-section which decreases in the direction of the said intermediate wall.

The second, upper section of the second sleeve 3b constitutes a locking male connection flange 12, for conical assembly of the "LÜER" type. Since a flange of this type is of a conventional sort, and in particular has a form and dimensions which are defined by standards, it will not be described in greater detail in the present application.

The injection device additionally comprises means for closing off the end of the cylindrical tube 1 of the syringe body, which can make it possible to allow injection of the liquid contained in the said tube.

These means for closing off comprise firstly a cylindrical stopper 13, which can be inserted in the cylindrical tube 1, and is provided with a cylindrical stop collar 14 on the end of the said tube.

This stopper 13 is additionally provided with a through cylindrical bore 15, which opens into a countersink 16 provided in the front surface of the said stopper, opposite the collar 14.

These means for closing off additionally comprise a unit 17 for closing off and distributing, which is designed to be accommodated in the bore 15 in the stopper 13, and extend inside the ring 3.

This unit 17 for closing off and distributing is in the general form of a shaft, comprising an intermediate flange 20, with a shape and dimensions which are conjugated with those of the upper compartment 8 of the second sleeve 3b of the ring 3.

The portion 17a of this shaft, which extends in the lower extension of the flange 20, has a cylindrical shape, with a diameter which is designed to penetrate in the bore 15 in the stopper 13.

The portion of this shaft 17 which extends in the upper extension of the flange 20 comprises a first cylindrical section 17b, with a diameter larger than that of the lower portion 17a of the said shaft, extended by a frusto-conical section 17c, with a form and dimensions which are suitable for constituting the conical end piece of the male locking connection of a "LÜER conical assembly".

The unit 17 for closing off and distributing is also provided axially, along its longest length, starting from its upper front surface, with a longitudinal duct 18, which opens into a through transverse duct 19 provided in the portion 17a of the shaft, at a short distance from the lower front surface of the said shaft.

The injection device additionally comprises a locking female connection 30, for conical assembly of the "LÜER" type. This conical connection 30, which is of a known type, conventionally comprises a conical base 23, in which there is crimped an injection needle 24, and, in the lower extension of the said base, a conical sleeve 21, which is conjugated with the conical end piece 17c of the male connection, which is provided with fins 22 which can permit screwing of the said female connection into the flange 12.

Finally, this injection device comprises a protective cap 25, with a shape which is designed to cover the base 23 of the female conical connection 30, and to accommodate the injection needle 24, the said protective cap comprising in a conventional manner an outer stop collar 26 on the flange 12.

Assembly of an injection device of this type consists simply, firstly, of introducing the unit 17 for closing off and distributing inside the ring 3, until the intermediate flange 20 is inserted in the upper compartment 8 of the said ring.

The stopper 13 is then also put into place in the ring 3, in a position in which the collar 14 of the said stopper is accommodated in the fourth section 6d of the first sleeve 3a of the said ring.

In this position of the stopper 13, and as represented in FIG. 1, the transverse duct 19 of the unit 17 for closing off and distributing is positioned in the bore 15 in the said stopper, recessed relative to the countersink 16 of the latter. In addition, this stopper 13 closes off at the front the lower compartment 7 of the ring 3, such as to limit the axial displacement of the unit 17 for closing off and distributing.

Finally, the last operation consists of presenting the syringe body opposite the above-described pre-assembled elements, and of fitting the said syringe body inside the ring 3, until the collar 2 of the cylindrical tube 1 clips into the toric intermediate section 6c of the first sleeve 3a of the said ring.

After the syringe body has been filled, and closed off by a piston body of the conventional type, the injection device can then be handled, stored etc., without any risk of escape of liquid, or of contamination of this liquid.

Figure 2:
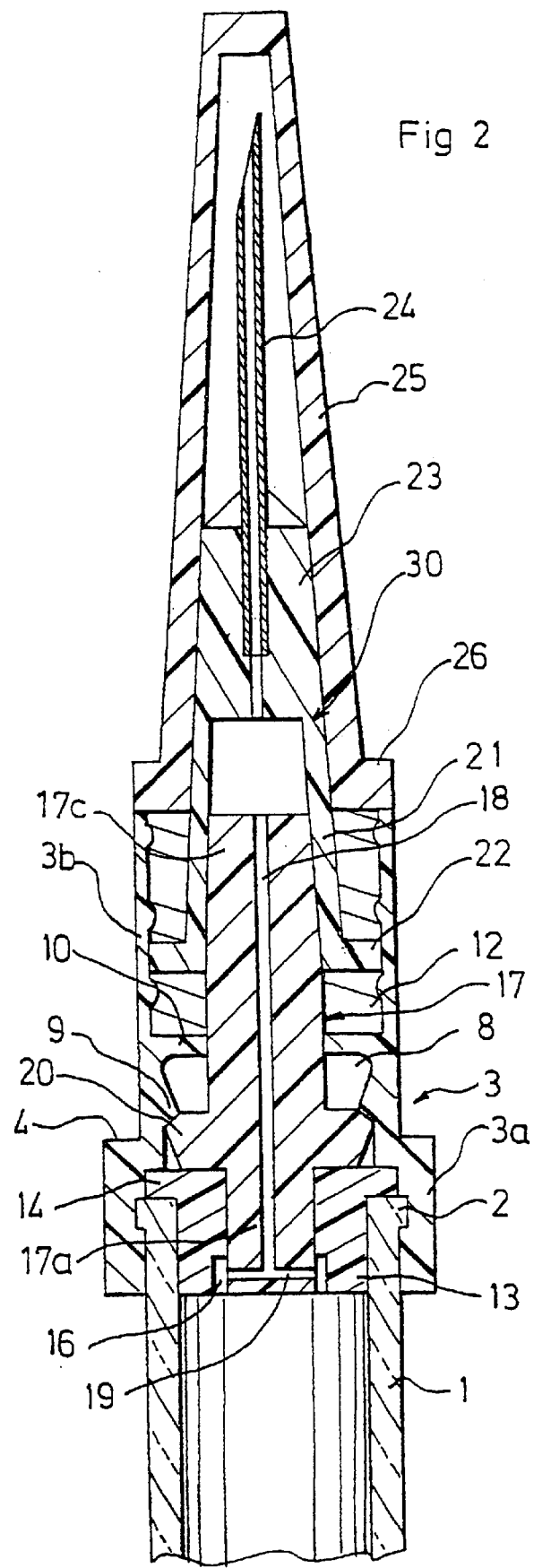
FIG. 2 is a longitudinal axial cross-section of this injection device after assembly of a female conical connection which supports an injection needle, which is protected by a protective cap.
Figure 3:
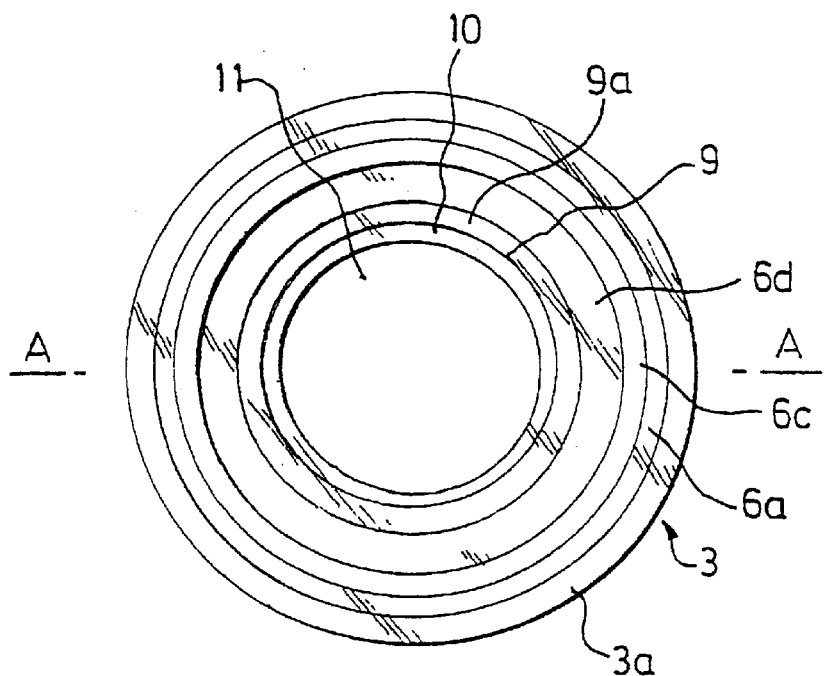
FIG. 3 is a front view from beneath, of the ring of the syringe body of this injection device.
Figure 4:
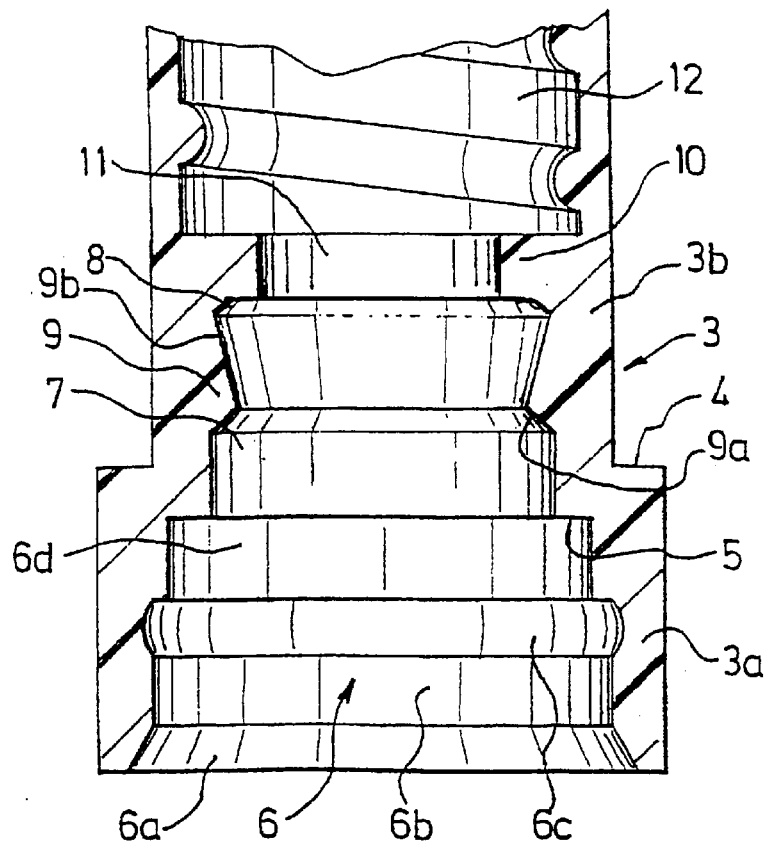
FIG. 4 is a longitudinal cross-section through an axial plane A of this ring.
Figure 5:
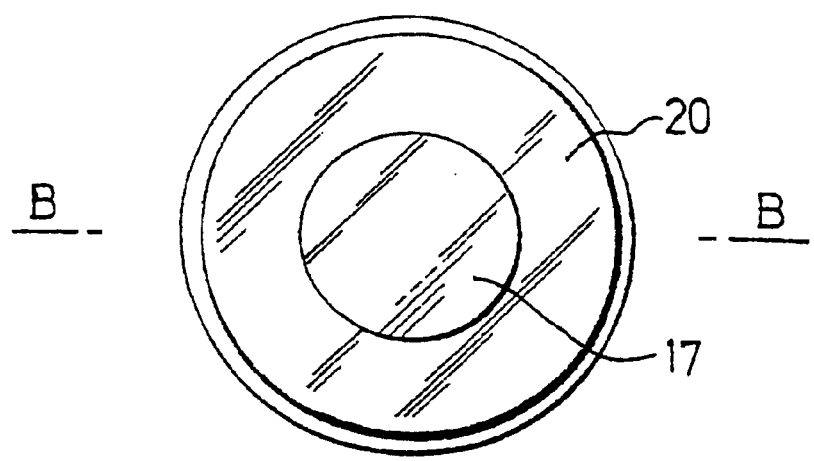
FIG. 5 is a front view from beneath, of the unit for closing off and distributing of this injection device.
Figure 6:
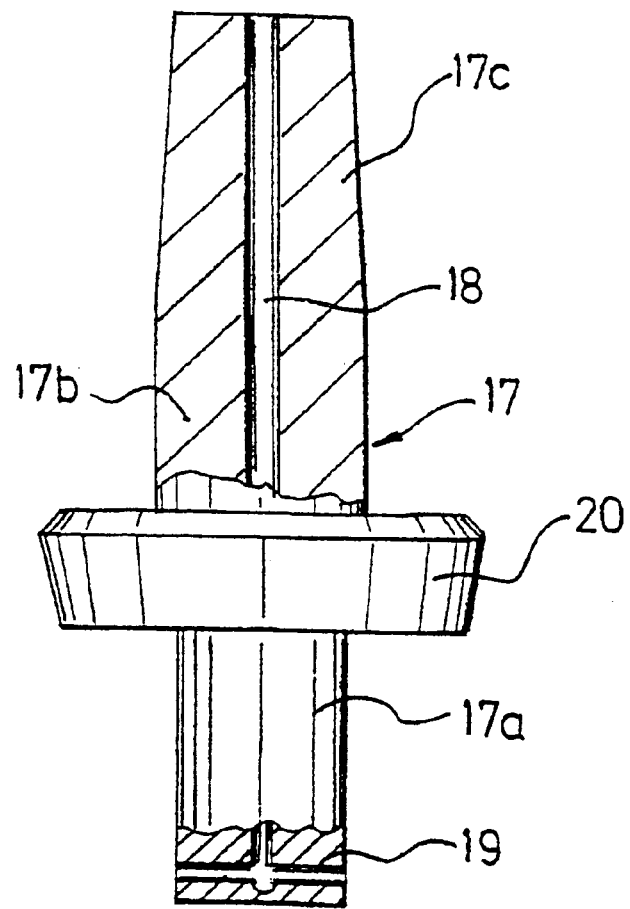
FIG. 6 is a longitudinal view partially in cross-section, through an axial plane B of this unit for closing off and distributing.

For the purpose of an injection, and as represented in FIG. 2, it is sufficient for the user to assemble the locking female conical connection 30 by screwing.

During this assembly, the unit 17 for closing off and distributing is automatically displaced axially towards an injection position, in which, firstly, the intermediate flange 20 is accommodated in the lower compartment 7 of the ring 3, and secondly, the transverse duct 19 opens into the countersink 16 in the stopper 13, thus permitting escape and injection of the liquid.

What is claimed is:

1. An injection device comprising a syringe body (1, 13), which delimits a chamber which is designed to be filled with a liquid and a unit (17) for closing off the chamber and distributing the liquid, comprising an end piece (17a) for closing off the said chamber, which is extended by a locking male conical connection (17c), provided with a duct (18, 19) for distribution of the liquid, the said unit for closing off and distributing being mobile axially between a position known as the closing-off position, in which the distribution duct (18, 19) is isolated from the chamber of the syringe body (1, 13), and a position known as the injection position, in which the said communication duct communicates with the said chamber, wherein, in the said injection device:

the unit (17) for closing off and distributing comprises an intermediate section (20), which is disposed between the closing-off end piece (17a) and the male conical connection (17c), and is placed such as to extend in an extension (3b) of the syringe body (1, 13);

the syringe body (1, 13) comprises a ring (3) which is provided with the extension (3b) and a front wall (10), in which there is provided an opening (11) for passage of the conical male connection (17c), the said ring:

delimiting two inner, upper (8) and lower (7) compartments which are juxtaposed axially, each of which has a shape which is conjugated with the intermediate section (20) of the unit (17) for closing off and distributing, and can accommodate the said intermediate section, the said compartments being separated by axial stop means (9) which can permit axial displacement of the intermediate section (20) of one compartment (7, 8) towards the other compartment (8, 7); and comprising in the extension of the front wall (10) a sleeve (12) which is threaded internally, and is designed to accommodate the male conical connection (17c) and to act as a fixed nut for assembly of a locking female conical connection (30) which supports an injection needle (24).

2. An injection device as claimed in claim 1, wherein the ring (3) has in its interior an annular neck (9) which forms the top of two longitudinal divergent sections (9a, 9b), and constitutes the axial stop means for separation of the upper (8) and lower (7) compartments, the intermediate section (20) of the unit (17) for closing off and distributing having a shape and dimensions which are conjugated with the upper compartment (8) of the said ring.

3. An injection device as claimed in claim 1, wherein:

the syringe body comprises a closing-off stopper (13) with dimensions which are suitable for being inserted in the syringe body, provided with a through bore (15) which opens into the said syringe body at a countersink (16); and the unit (17) for closing off and distributing has dimensions which are designed to be inserted in the bore (15) in the closing-off stopper (13), and comprises the distribution duct (18, 19) containing a transverse branch (19), which is disposed such as to be positioned recessed from the countersink (16) in the said closing-off stopper (13), in the closing-off position of the unit (17) for closing off and distributing, and to extend into the said countersink, in the injection position of the said unit.

* * * * *